(12) United States Patent
Petersen et al.

(10) Patent No.: US 9,567,138 B2
(45) Date of Patent: Feb. 14, 2017

(54) DELIVERY SYSTEM

(75) Inventors: Christina M. Petersen, Elgin, IL (US); Marcy E. Freeman, Highland Park, IL (US)

(73) Assignee: SUNSTAR AMERICAS, INC., Chicago, IL (US)

( * ) Notice: Subject to any disclaimer, the term of this patent is extended or adjusted under 35 U.S.C. 154(b) by 696 days.

(21) Appl. No.: 13/479,519

(22) Filed: May 24, 2012

(65) Prior Publication Data

US 2012/0301851 A1 Nov. 29, 2012

Related U.S. Application Data

(60) Provisional application No. 61/489,596, filed on May 24, 2011.

(51) Int. Cl.
*B65D 35/38* (2006.01)
*B65D 47/08* (2006.01)

(52) U.S. Cl.
CPC .......... *B65D 47/0814* (2013.01); *B65D 35/38* (2013.01); *A61K 2800/87* (2013.01); *A61K 2800/88* (2013.01)

(58) Field of Classification Search
CPC ... B65D 35/38; B65D 47/0814; B65D 77/044; A61Q 11/00; A45D 44/18; A45D 33/00
USPC ... 206/277, 229, 223; 222/92, 572; 132/286; 424/49; 433/216
See application file for complete search history.

(56) References Cited

U.S. PATENT DOCUMENTS

| | | | | |
|---|---|---|---|---|
| 1,980,473 A * | 11/1934 | Coffelder | ........ | 222/322 |
| 2,393,103 A * | 1/1946 | Groedel | ........ | 206/216 |
| 3,054,505 A * | 9/1962 | Hennessey | ........ | 206/216 |
| 3,378,137 A * | 4/1968 | Stone | ........ | 206/277 |
| 3,684,085 A * | 8/1972 | Desmond | ........ | 206/277 |
| 3,797,648 A * | 3/1974 | Shaw | ........ | 206/277 |
| 4,119,203 A * | 10/1978 | Kuchenbecker | ........ | 206/461 |
| 4,300,682 A * | 11/1981 | Kuchenbecker | ........ | 206/461 |
| 4,796,783 A * | 1/1989 | Paulson | ........ | 222/80 |
| 4,957,202 A * | 9/1990 | Yoshiki et al. | ........ | 206/734 |
| 5,052,589 A * | 10/1991 | O'Meara | ........ | 222/83 |
| 5,279,813 A * | 1/1994 | Gaffar et al. | ........ | 424/49 |
| 5,547,091 A * | 8/1996 | Neveras et al. | ........ | 215/237 |
| 5,816,451 A * | 10/1998 | Renault | ........ | 222/215 |
| 6,112,893 A * | 9/2000 | Aubry et al. | ........ | 206/277 |
| 6,484,876 B1 * | 11/2002 | Duqueroie | ........ | 206/277 |
| 7,040,499 B1 * | 5/2006 | Reif | ........ | 220/291 |
| 8,096,448 B2 * | 1/2012 | Keller et al. | ........ | 222/107 |
| 2003/0053972 A1 | 3/2003 | Newell | | |
| 2007/0000943 A1 * | 1/2007 | Morgan | ........ | 222/107 |
| 2007/0009447 A1 * | 1/2007 | Gadkari et al. | ........ | 424/49 |
| 2007/0187429 A1 * | 8/2007 | Farahmand | ........ | 222/94 |
| 2007/0267436 A1 * | 11/2007 | Abbott et al. | ........ | 222/94 |

(Continued)

OTHER PUBLICATIONS

GoSMILE AM/PM Duo Pack, http://www.amazon.com/GoSMILE-Duo-Pack-Maintenance-Aromatherapy/dp/B000SQUIBW/ref=sr_1_1?ie=UTF8&qid=1427816323&sr=8-1&keywords=gosmile+am%2Fpm+duo+pack. Jul. 9, 2007.*

(Continued)

*Primary Examiner* — Steven A. Reynolds

(74) *Attorney, Agent, or Firm* — Michael Best & Friedrich LLP

(57) ABSTRACT

Provided herein is a toothpaste composition, tube, and delivery system/kit. The disclosure also provides methods for use of the toothpaste composition and/or delivery system/kit.

15 Claims, 13 Drawing Sheets

(56) References Cited

U.S. PATENT DOCUMENTS

| | | |
|---|---|---|
| 2008/0105328 A1* | 5/2008 | Desmond .......................... 141/2 |
| 2008/0135429 A1 | 6/2008 | Wright |
| 2008/0248073 A1 | 10/2008 | Gantenberg |
| 2009/0008271 A1* | 1/2009 | Zimmer et al. .............. 206/63.5 |
| 2009/0139884 A1* | 6/2009 | Kim .............................. 206/277 |
| 2010/0224633 A1* | 9/2010 | Gelardi ......................... 220/315 |
| 2014/0202919 A1* | 7/2014 | Van Meeteren .............. 206/581 |

OTHER PUBLICATIONS

International Search Report and Written Opinion for Application No. PCT/US2012/039464 dated Nov. 26, 2012 (9 pages).

* cited by examiner

DELIVERY SYSTEM

CROSS-REFERENCE TO RELATED APPLICATIONS

This application claims the benefit of and priority to U.S. Provisional Patent Application No. 61/489,596, filed May 24, 2011, the entire contents of which are hereby incorporated by reference.

BACKGROUND

Toothpastes and other dentifrices typically include fluoride as an active agent (e.g., to prevent tooth decay, formation of dental caries). While topical administration of fluoride to teeth can reduce tooth decay, fluoride can be harmful if ingested. When brushing teeth the consumption of fluoride by children can be a particular concern because, due their relatively small body mass, the quantity of fluoride they may ingest (inadvertently or purposefully) is proportionally greater compared to the amount an adult may ingest.

Children may also object to practicing a routine for brushing their teeth. Prior attempts to encourage brushing have included development of toothpaste flavors that appeal to children. However, because of the better flavor, children may intentionally or unintentionally swallow substantial amounts of toothpaste. Moreover, children generally do not understand that it is not proper to swallow toothpaste and might swallow large amounts even though many children's toothpastes include a warning label against ingestion of the product. Much of the problem stems from the tendency of children to apply too much toothpaste onto the brush.

In response to these concerns, toothpaste manufacturers generally recommend that children use only a pea-size quantity of toothpaste on the brush. While such warnings are certainly proper, they are often not understood and ignored by both children and adults who assist children in brushing their teeth, alike. Similarly, certain toothpaste formulations intended for adult use may require adults to limit the amount of toothpaste composition that used and that may be applied to a brush; however adults may not read instructions for application and use or may simply not appreciate the importance of regulating the amount of product used in such situations. Thus, when brushing teeth, adults and children will often apply a solid strip of toothpaste across the entire length of the toothbrush bristles, creating the potential for ingesting elevated amounts of fluoride or other actives that may cause deleterious effects.

Accordingly, toothpaste formulations, delivery systems (e.g., tubes), and kits that are able to control the amount of toothpaste applied to a toothbrush and/or can induce or encourage a child to comply with a regular brushing routine and/or assist adults in dispensing proper amounts of product on a toothbrush would be of great benefit.

SUMMARY

In an aspect, the disclosure provides a children's toothpaste delivery kit comprising a plurality of tubes, wherein at least two tubes in the plurality of tubes comprises a toothpaste having at least one unique property relative to the toothpaste comprising the other of the plurality of tubes.

In another aspect, the disclosure provides a toothpaste tube comprising a deformable material, the tube having a substantially elongated shape generally tapering at one end to define a nozzle. The opening of the nozzle is sized to be smaller than the width of the typical toothbrush head, and such that it allows for control of (or regulates) the amount of toothpaste, or similar material, that can be dispensed by the user.

In another aspect, the disclosure provides a toothpaste composition comprising a flavoring agent, a coloring agent, a humectant, an abrasive, a buffering agent, a binder, a sweetener, and water, wherein the composition comprises a viscosity of about 30,000 to about 300,000 cps (at ~25° C.) and/or a specific gravity of about 1.20 to about 1.40 (at ~25° C.).

In another aspect, the disclosure provides a toothpaste delivery kit having a first tube containing a first product, a second tube containing a second product where the first product has at least one property different from the second product, and a package at least partially containing the first tube and the second tube therein. In some embodiments the first and second products comprise a gel or paste. In further embodiments the gel or paste is formulated for application to oral tissue (e.g., teeth, tongue, palate, and/or gums).

In another aspect, the disclosure provides a nozzle for use with a body containing a paste-like substance. The nozzle having a substantially conical body defining a channel therethrough, the channel including a threaded portion, a collection chamber, and an output orifice defining a output diameter where the output orifice is between about 0.04 inches and about 0.2 inches in diameter.

In another aspect, the disclosure provides a toothpaste tube having a substantially elongated tube formed from flexible material, a nozzle coupled to the tube having a substantially conical body defining a channel therethrough. The channel including a threaded portion, a collection chamber, and an output orifice defining an output diameter, and where the output diameter is between about 0.04 and about 0.2 inches.

In another aspect, the disclosure provides a method of cleaning the oral cavity of a user. In some embodiments, the method provides for cleaning of one or more teeth and/or gums. In embodiments, the method comprises providing a first product having a first property, providing a second product having a second property different from the first property of the first product, wherein combining the first product with the second product on the bristles of a toothbrush produce a third property different from the first and second properties, and applying the combined first and second products to the oral cavity of a user.

The disclosure provides for and encompasses additional aspects and embodiments, which will be apparent to those of skill in the art in light of the following description.

DETAILED DESCRIPTION

Figure 1:
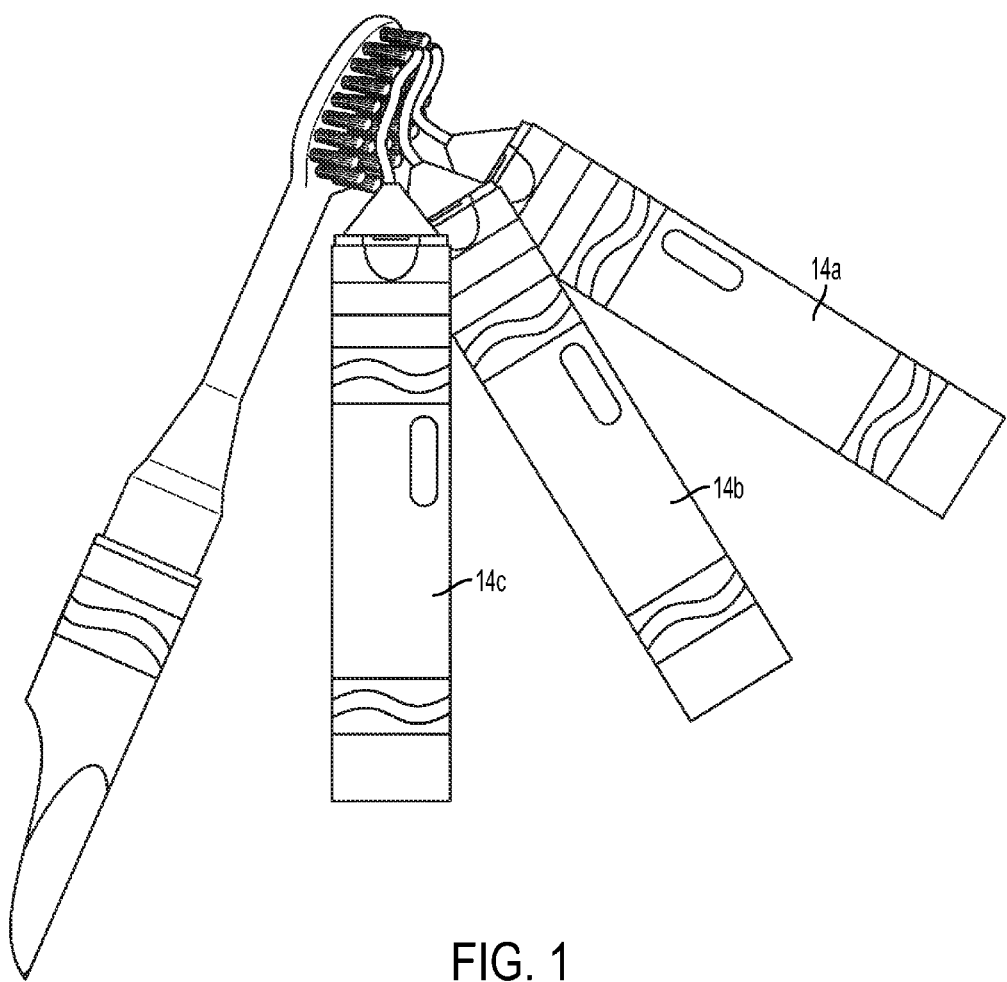
FIG. 1 depicts a non-limiting example of a toothpaste formulation, tube, and delivery system/kit as described herein.

In a general sense, the disclosure relates to toothpaste formulations, toothpaste tubes, toothpaste delivery systems (e.g., kits) and methods for using the same. As described herein, the various aspects of the disclosure can aid in developing and encouraging children and adults to adopt and comply with a proper oral hygiene routine that includes regular tooth brushing, while also helping to control the amount of toothpaste that is applied to the brush. The formulations, tubes, and kits allow a user to exert more control over the tooth brushing routine, which can make the experience more interactive, exciting, fun, and enjoyable, encourages continued compliance, and can provide for proper product use (e.g., dispensing recommended/proper amount of product).

As used herein, the phrase "effective amount", relates to an amount of a substance sufficient to provide the desired benefit without undue adverse side effects, such as toxicity, irritation, or allergic response, commensurate with a reasonable benefit/risk ratio when used in the manner of this invention.

The term "toothpaste" or "product" as used herein, includes any paste or gel compositions which can be generally used when brushing the teeth.

In an aspect, the disclosure provides a toothpaste delivery kit. FIGS. 1-12 illustrate non-limiting embodiments and components of a toothpaste delivery kit 10 for use by children or adults to promote proper dental hygiene and clean teeth. The kit (10) includes one or more (e.g., one, two, three, four, five, six, etc.) toothpaste tubes 14a, 14b, 14c, each of which are placed in a container or package 18 for sale or distribution. In the illustrated construction, each tube 14a, 14b, 14c of the toothpaste delivery kit 10 is filled with product (e.g., toothpaste, gel, etc.) that has one or more unique properties as compared to the product contained in the other tubes of the kit 10 giving the user the ability to mix and match the variations of toothpaste. These properties may include, but are not limited to, color, texture, flavor, extrusion shape, and the like. In the illustrated construction, each tube 14a, 14b, 14c contains product that includes a unique color/flavor combination that can be generated based on common color and flavor associations, market research, or the like (e.g., red selected from cherry, bubblemint, fruit punch, etc.; yellow selected from lemon, banana, etc.; green selected from lime, apple, watermelon, etc.; blue selected from blueberry, mixed berry, etc.). Although not illustrated, the kit 10 may also include one or more toothpaste accessories such as toothbrushes, floss, other dentifrices (e.g., mouthwash, powders), and the like.

Figure 3:
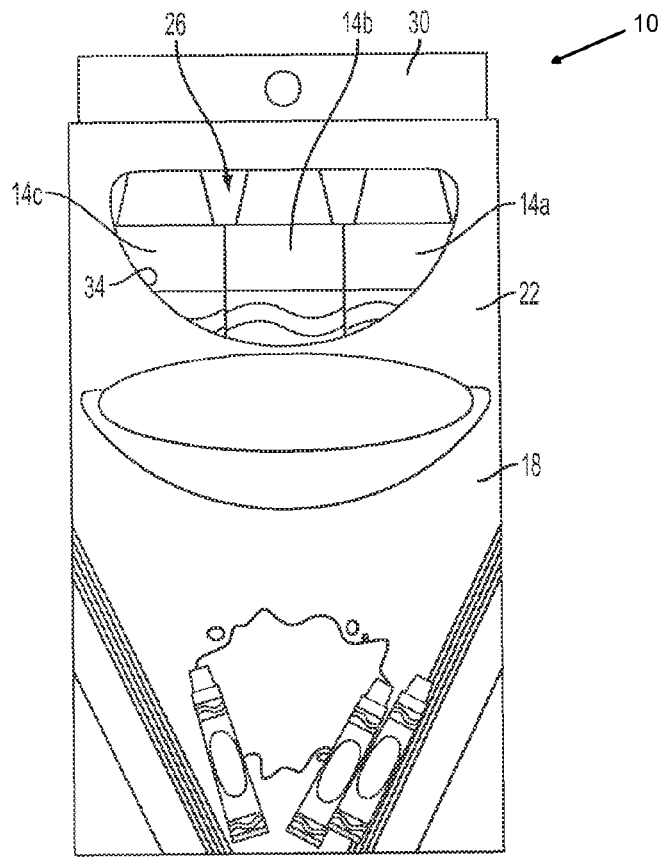
FIG. 3 depicts one embodiment of packaging for the delivery system of FIG. 1.
Figure 3A:
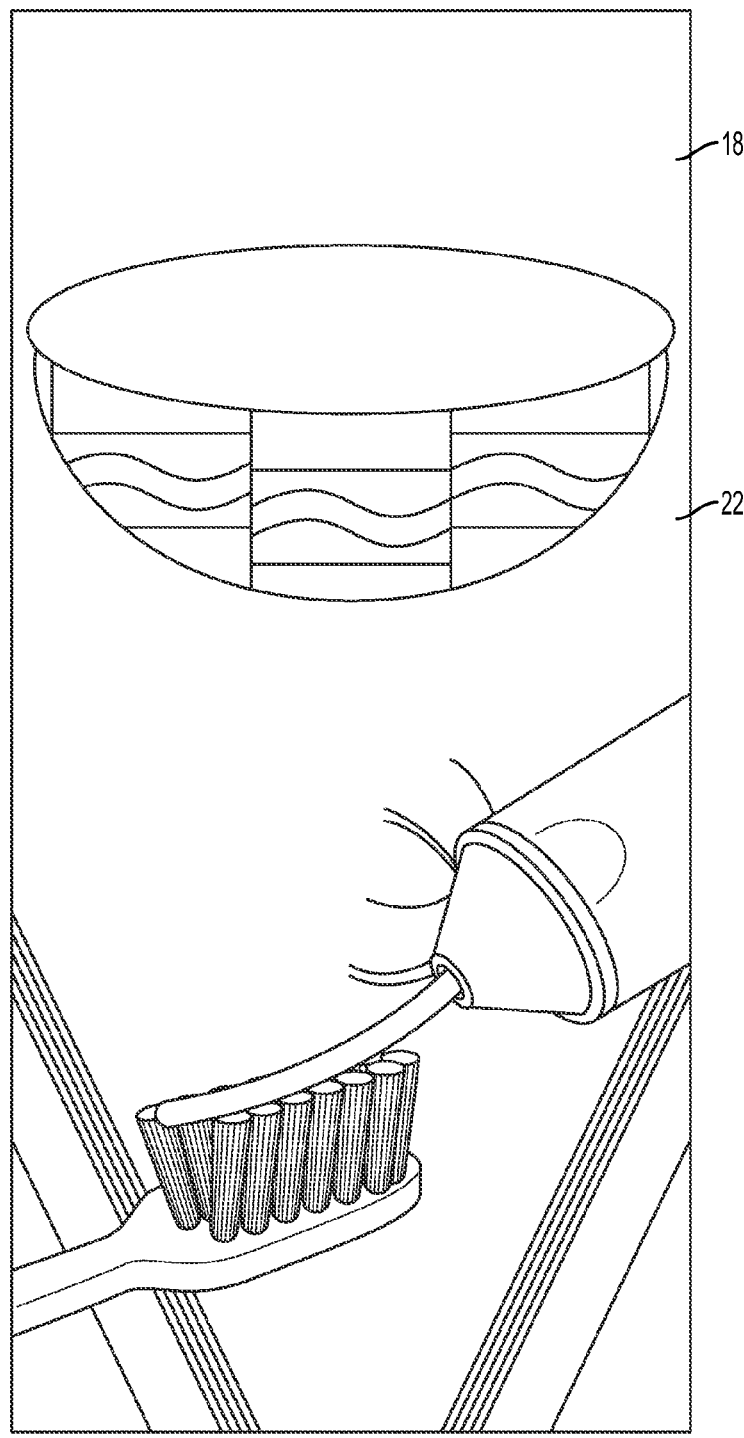
FIG. 3A depicts the packaging embodiment of FIG. 3 without an aperture.
Figure 3B:
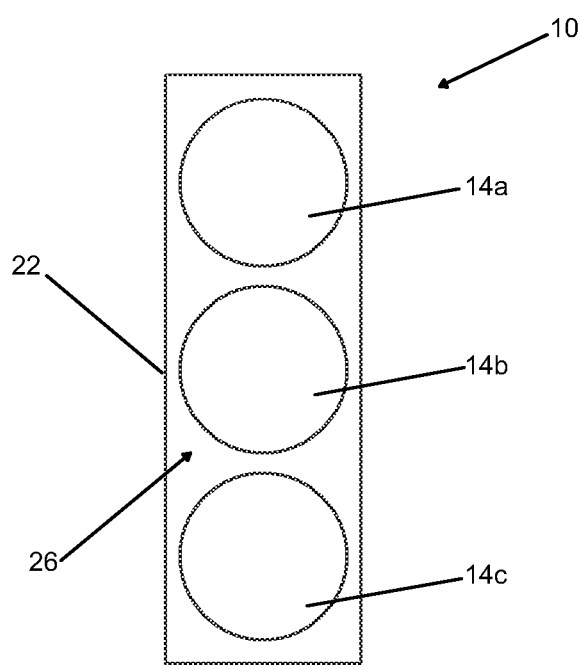
FIG. 3B is a section view of the packing embodiment of FIG. 3.
Figure 5:
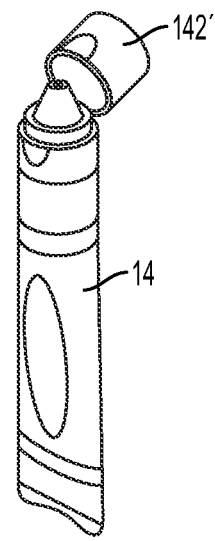
FIG. 5 depicts a tube from a toothpaste delivery system having another embodiment of a nozzle attached thereto.
Figure 6:
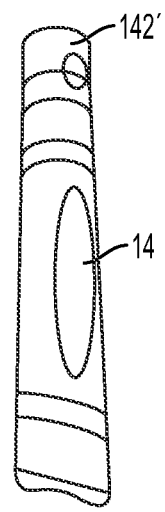
FIG. 6 depicts the tube from FIG. 5 with the nozzle in the closed position.
Figure 7:
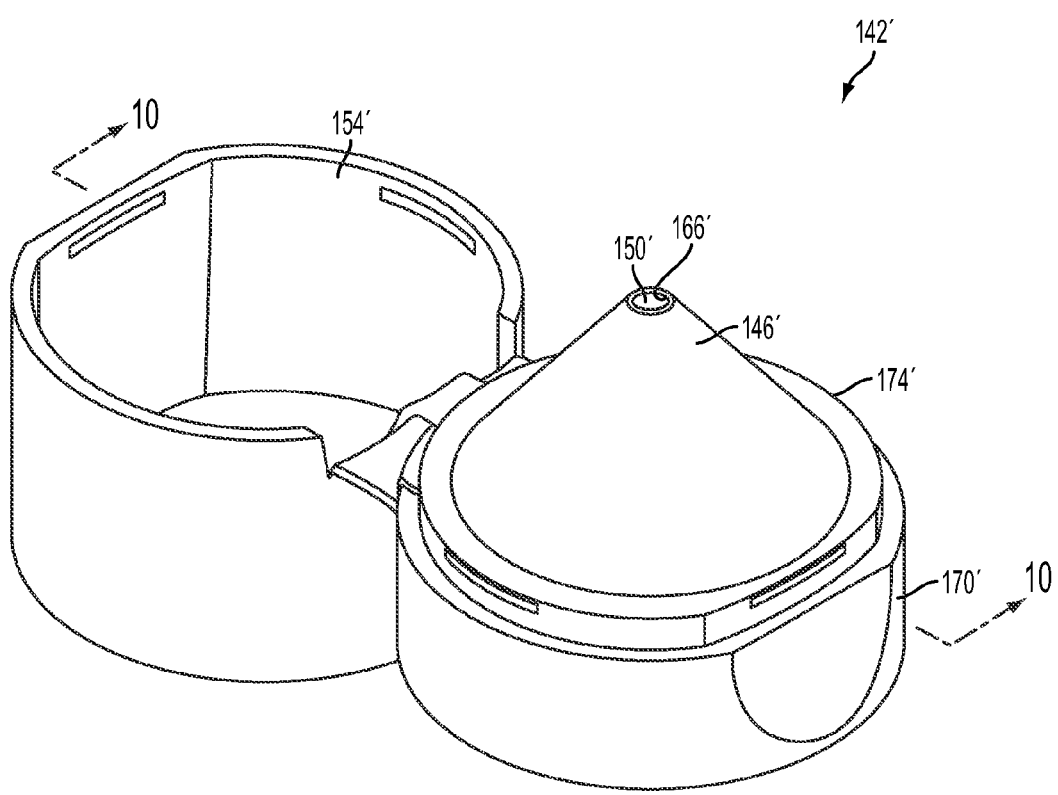
FIG. 7 depicts an embodiment of a nozzle.
Figure 8:
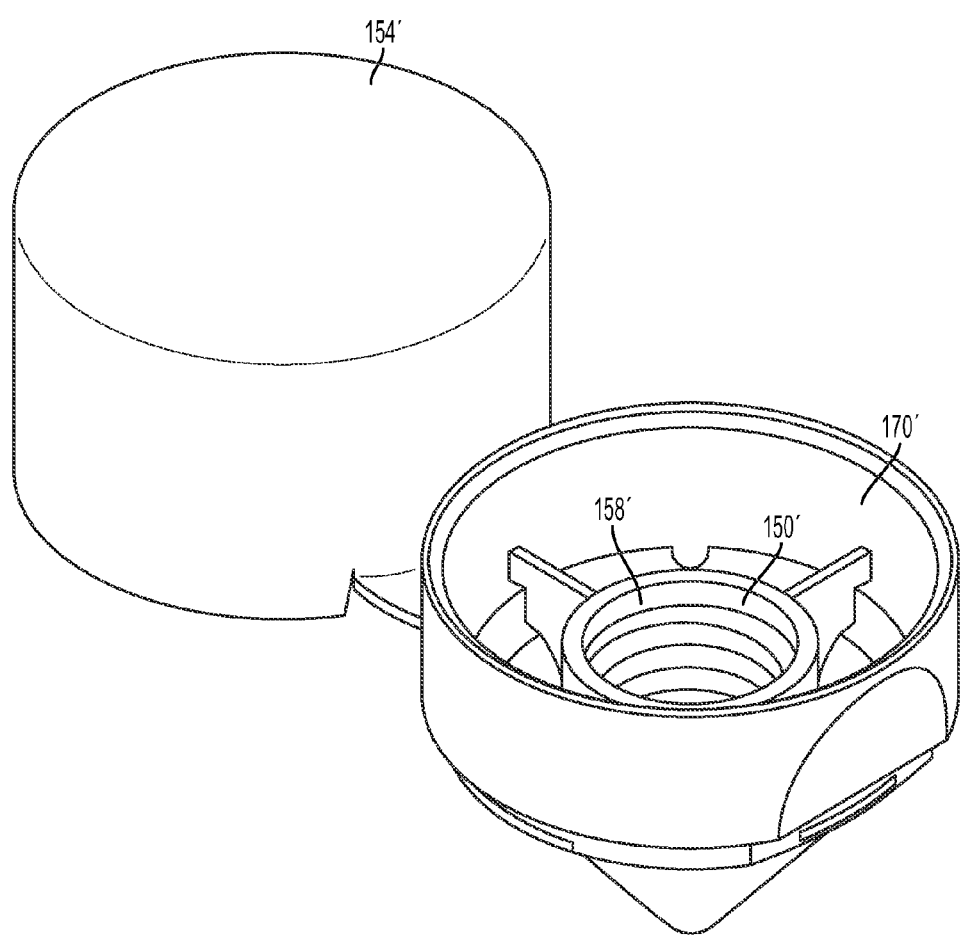
FIG. 8 depicts an embodiment of a nozzle.

FIGS. 3-3B show a first embodiment of the package 18, which is generally rectangular in shape and has a plurality of walls 22 defining a storage volume 26 therebetween. The package 18 also includes a tab 30 extending therefrom to allow the package 18 to be hung from a hook for display. When assembled, each of the tubes 14a, 14b, 14c are placed within the storage volume 26 in a substantially linear fashion such that each tube 14a, 14b, 14c is at least partially visible through an aperture 34 (when present) formed in the front wall 22 of the package 18 (see FIG. 3). The package 18 also includes indicia printed thereon to promote the product, as well as to provide, e.g., the illusion of a crayon box. In some embodiments, the package can have a generally rectangular shape with dimensions proportioned to fit one, two, three, four, or five or more tubes disclosed herein. In some embodiments, the overall dimensions can vary between about 2¾" to about 3½" (width); about 1" to about 1½" (thickness/depth); and about 5¼" to about 6¾" (length/height). In one embodiment, the rectangular package 18 has overall dimensions of about 3¼"×1½"×5½". In one embodiment, the rectangular package 18 has overall dimensions of about 3⅛"×1⅛"×6½". In still other embodiments, the package 18 may not define an aperture (FIG. 3A). Another embodiment of the rectangular package can be found in FIG. 12.

Figure 4:
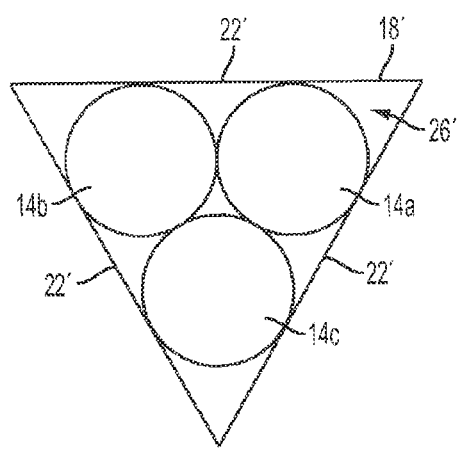
FIG. 4 depicts another embodiment of packaging for the delivery system of FIG. 1.

Illustrated in FIG. 4, a second embodiment of the package 18' is generally triangular in shape, having a plurality of walls 22' defining a storage volume 26' therebetween. Similar to the first embodiment, the second embodiment of the package 18' may include a tab (not shown) extending therefrom to allow the package 18' to be hung from a hook for display. When assembled, each of the tubes 14a, 14b, 14c are placed within the storage volume 26' in a generally triangular orientation (see FIG. 4). As such, the second embodiment of the package 18' allows the same number of tubes to be displayed as the first embodiment 18, but uses less overall width in the display area. One example of the triangular construction has overall dimensions of 2½"×2½"×5½".

The illustrated packaging can be associated with a particular theme that is appealing to children (e.g., cartoon characters, celebrities, TV shows, activities, and the like). For example, the embodiments illustrated in FIG. 1 mimic the look and feel of coloring by using toothpaste with vivid colors and a container that looks like a small package of crayons.

Figure 1A:
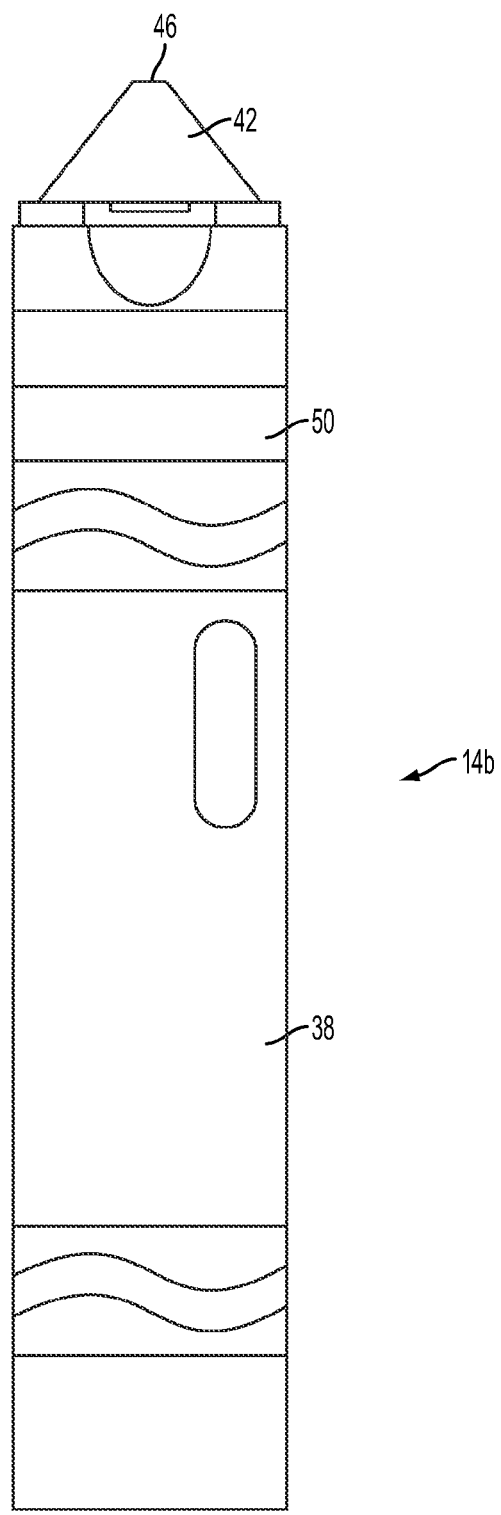
FIG. 1A depicts a tube from the delivery system of FIG. 1.

Illustrated in FIG. 1A, each tube 14a, 14b, 14c of the toothpaste delivery kit 10 includes a body 38 and a nozzle 42 coupled to one end of the body 38. The body 38 of the tube is generally formed from flexible laminate, or other similar material, to minimize moisture transmission. During use, the user can squeeze or manipulate the body 38 causing it to force the product from the nozzle 42 and onto the bristles of a toothbrush. More specifically, the user must apply at least a dispensing force to the body 38 before the product will be dispensed from the tube. The dispensing force can be modified by changing any combination of the stiffness of the material forming the body 38, the viscosity of the product contained within the tube, and the size and shape of the nozzle 42.

The body 38 also includes indicia printed thereon corresponding to the product contained therein. The indicia is generally color coded to correspond to the color and/or flavor of product contained within the tube. In the illustrated construction, the indicia also includes markings causing the tube to resemble a crayon. Other themes may be used where desired.

In some embodiments, the nozzle 42 of each tube may be substantially elongated in shape, one end of which is tapered. The nozzle has an opening 46, which is sized to be smaller than the width of a toothbrush head (see FIG. 1) so the user can apply multiple thin ribbons or beads of toothpaste to the bristles located on the head. In the illustrated embodiment, the nozzle 42 defines an orifice diameter between about 0.04" and about 0.2". Other embodiments provide a nozzle 42 with an orifice diameter between about 0.04" and about 0.1". Still other embodiments provide a nozzle 42 with an orifice diameter between about 0.04" and about 0.06". The illustrated embodiment defines an orifice diameter of about 0.06". Typical existing toothpaste tube designs generally define an orifice diameter of about 0.28" to about 0.32". The orifice diameter of the nozzle 42 can be tailored to the viscosity of the product it contains, so as to produce the desired dispensing characteristics. Furthermore, the nozzle 42 of the illustrated construction may be approximately 1" long.

In alternate constructions and embodiments, the opening 46 of the nozzle 42 may be formed in a unique cross-sectional shape, such as a triangle, star, heart, square and the like (not shown). As such, when product is dispensed from the nozzle 42, the product is extruded in a similar, unique shape. As described above, the nozzle 42 for each tube 14a, 14b, 14c within the kit 10 may form a different, unique cross-sectional shape.

The nozzle 42 also includes a shoulder 50, opposite the opening 46 that expands radially outwardly to a produce a shoulder diameter to which the body 38 is attached. In some constructions and embodiments, the shoulder diameter may be anywhere from about ½" to about 2". Alternative toothpaste tube designs well know in the art (not shown) generally have a shoulder diameter between about 0.95" and about 1.33".

Figure 2:
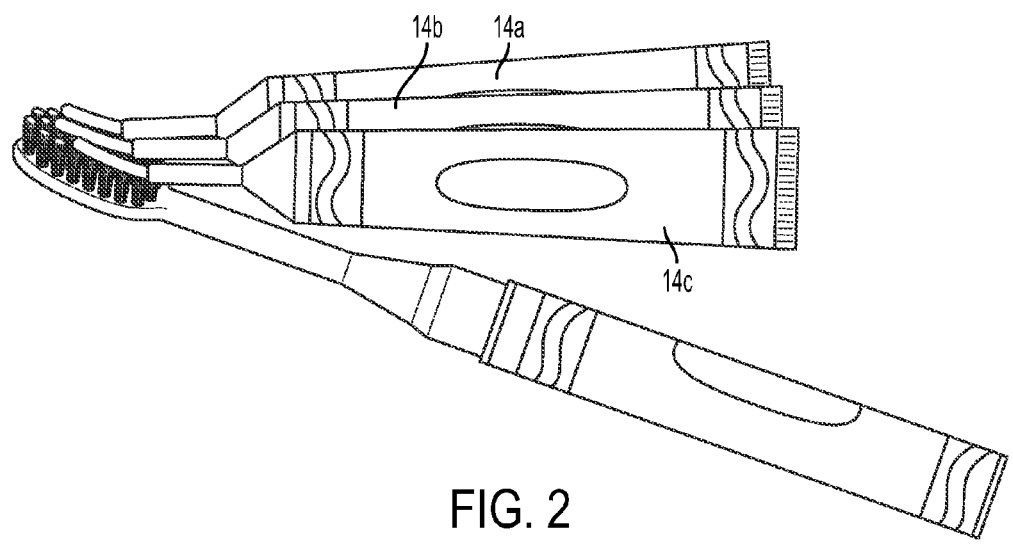
FIG. 2 depicts a non-limiting example of a toothpaste formulation tube, and delivery system/kit as described herein.
Figure 2A:
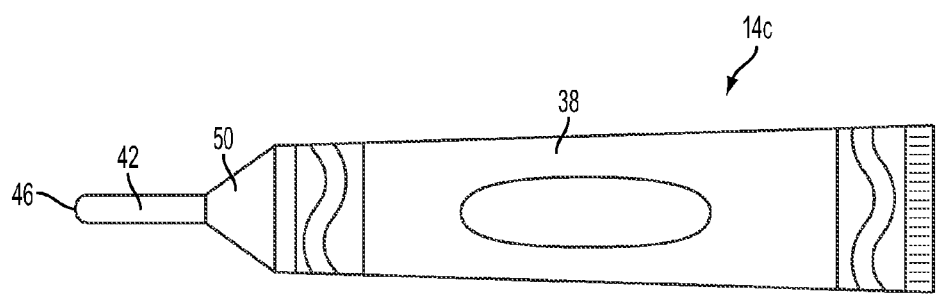
FIG. 2A depicts a tube from the delivery system of FIG. 2.

Another embodiment of the kit is shown in FIGS. 2 and 2A.

Other non-limiting embodiments of the nozzle 142' are illustrated in FIGS. 5-11. The nozzle 142' is an independent unit couplable to a tube 14 for use (see FIGS. 5-6). The nozzle 142' includes a substantially conical body 146' defining a channel 150' therethrough, and a cap 154' coupled to the body 146' and moveable between an open position (see FIG. 5) and a closed position (see FIG. 6). In the illustrated embodiments, when the cap 154' is in the open position, the body 146' of the nozzle 142' is designed to resemble the top portion of a crayon or similar writing or drawing implement.

Figure 9:
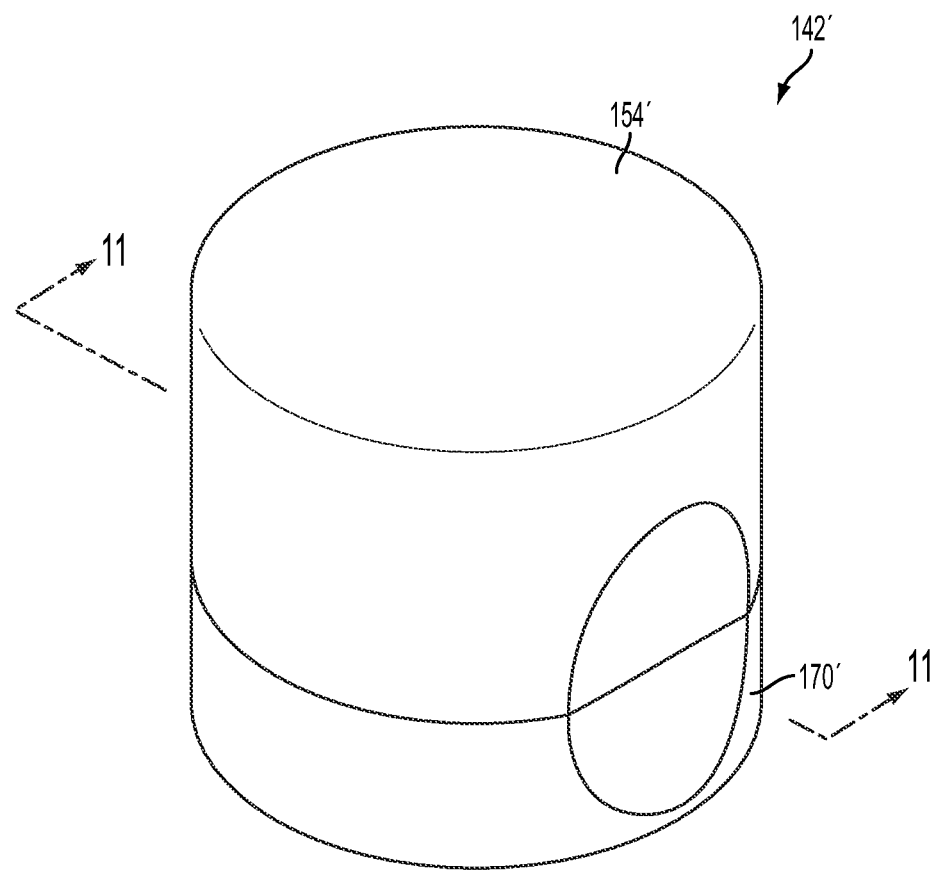
FIG. 9 depicts an embodiment of a nozzle.
Figure 10:
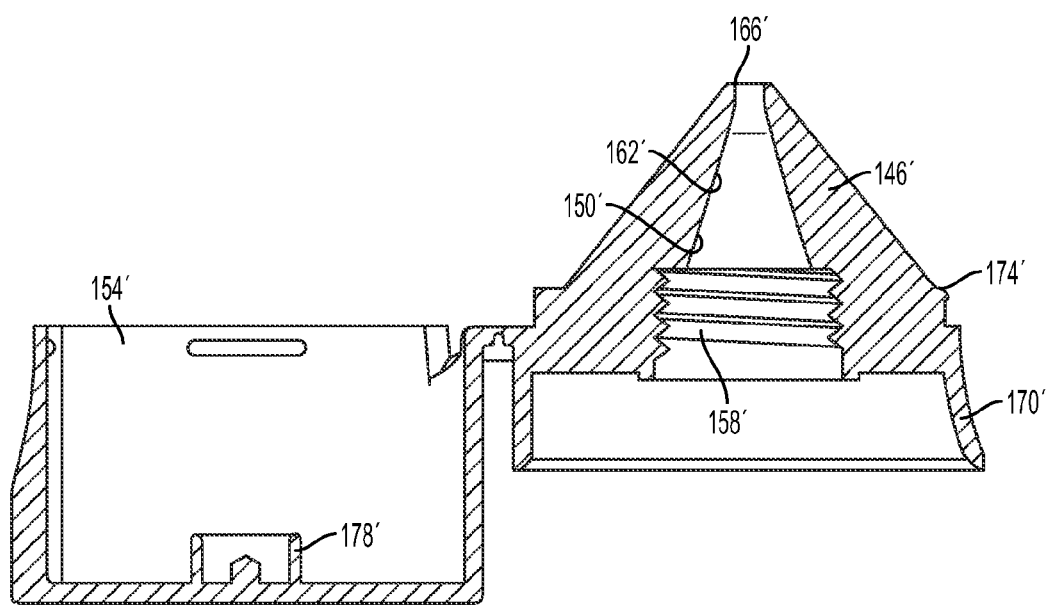
FIG. 10 is a section view taken along lines 10-10 of FIG. 7.
Figure 11:
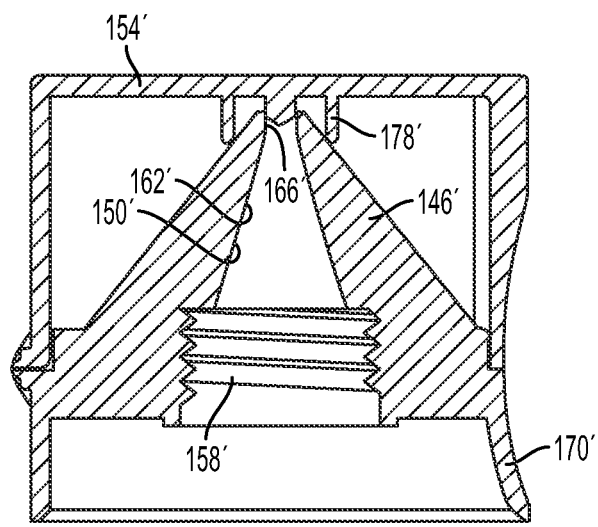
FIG. 11 is the section view taken along line 11-11 of FIG. 9.
Figure 12:
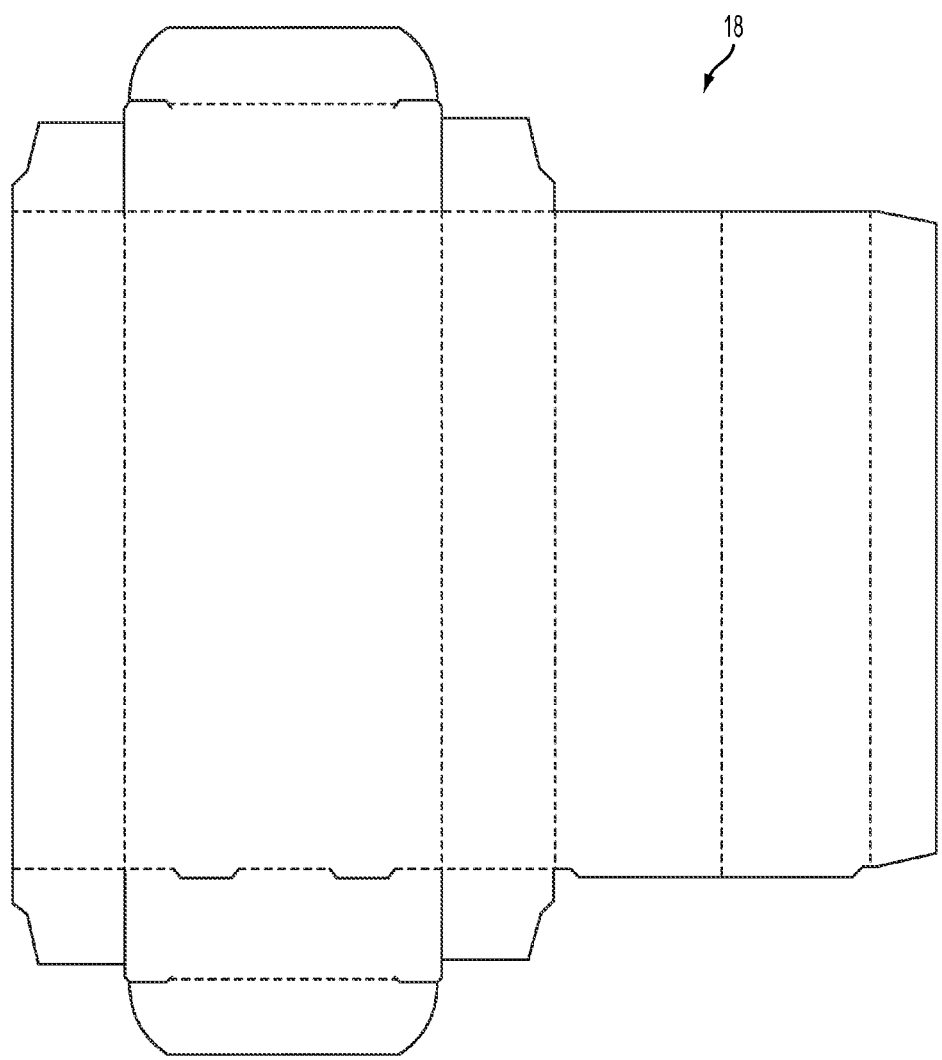
FIG. 12 depicts one embodiment of packaging for the kit/delivery system as herein described.

Illustrated embodiments in FIGS. 9-11, depict the channel 150' as including a threaded portion 158', a collection chamber 162', and an output orifice 166'. When assembled, the threaded portion 158' of the channel 150' is couplable to the tube 14 for use therewith. The collection chamber 162' of the channel 150' is substantially cylindrical in shape and extends from the threaded portion 158' to define an output orifice 166' opposite the threaded portion 158'. In the illustrated construction, the collection chamber tapers as it extends between the threaded portion 158' and the output orifice 166'.

The output orifice 166' of the present invention is substantially circular in shape and defines a diameter between about 0.04 and about 0.2 inches in diameter. In other constructions, the diameter may be between about 0.04 and about 0.1 inches. In yet another embodiment, the diameter may be between about 0.04 and about 0.06 inches. In the illustrated construction, the orifice is 0.06 inches in diameter. The size and shape of the orifice 166' can be selected to allow more precise control of the product being dispensed, thereby allowing the user to place multiple thin ribbons or beads of product on a single brush head (described below). Stated differently, the orifice 166' is tailored to the specific gravity and viscosity of the product contained within the tube 14. In alternate constructions, the orifice 166' may also be tapered or include a beveled edge. Such construction can allow for the controlled dispensing of the product (i.e., preventing excess product application).

When in use, the diameter of the output orifice 166' is sized to be less than half of the head width of a standard child- or adult-sized toothbrush where the head width is defined as the portion of the toothbrush with a plurality of bristles attached thereto and the width is the widest portion of the head measured perpendicular to the elongated axis of the brush. As such, more than one thin ribbon or bead of product may be applied to the head of the brush at a single time.

The nozzle 142' also includes a shroud or annular wall 170' extending from the bottom of the body 146' to enclose the threaded portion 158' of the channel 150'.

The nozzle 142' also includes a ridge 174' extending around the base of the body 150' proximate the shroud 170'. The ridge 174' contacts and helps position the cap 154' when in the closed position (FIG. 11).

Illustrated in FIGS. 10 and 11, the cap 154' includes a plug 178' having a protrusion and an annular wall. When the cap 154' is in the closed position, the plug 178' is configured to interact with and effectively seal the output orifice 166' of the nozzle 142'.

To brush, the kit 10 may be used in the following manner. The user (e.g., an adult or child) removes one or more of the tubes 14a, 14b, 14c from the packaging 18. The user then selects a first tube (e.g., tube 14a) having product with a first color and a first flavor. The user then removes the cap from the nozzle 42 and applies a first thin ribbon or bead of product to the brush head (e.g., by applying the necessary distribution force to the body 38 of the tube 14a). The user may then select a second tube (e.g., tube 14b) containing product with a second color and a second flavor different from the first color and the first flavor. The user removes the cap from the nozzle 42 and may apply a second thin ribbon or bead of product to the brush head adjacent the first thin ribbon or bead. The user may then continue to apply additional thin ribbons or beads of product to the brush head as desired from any of the tubes 14a, 14b, 14c.

The user then proceeds to brush his or her teeth causing the thin ribbons or beads of product to mix. This mixture results in a unique color/flavor combination that can be tailored by the user for each use dependent upon the amount and combination of colors and flavors (e.g., tubes) that are used. For example, if a first thin ribbon or bead of green/lime is applied along with a second thin ribbon or bead of yellow/lemon, the user will produce a lemon-lime flavor and a light green color. As will be appreciated by one of ordinary skill in the art, any type of color and flavor combination falls within the scope of the disclosure.

One embodiment of a toothpaste composition comprises a flavoring agent, a coloring agent, a humectant, an abrasive, a buffering agent, a binder, a sweetener, and water. In some embodiments the composition can further comprise an effective amount of fluoride. In some embodiments the composition can further comprise a preservative. The toothpaste composition is suitably formulated so that it can generally maintain its general size and shape upon extrusion from a container (e.g., a tube as described herein, or otherwise known in the art) onto a toothbrush, and can further remain substantially on top of the brush bristles (i.e., does not sink into the brush bristles). Thus, in some embodiments the toothpaste is formulated to have a viscosity of about 30,000 to about 300,000 cps (at ~25° C.) and/or a specific gravity of about 1.20 to about 1.40 (at ~25° C.). Thus some embodiments, as described in further detail herein, provide for a toothpaste (including a gel) having a characteristic color and flavor/odor, that can be extruded as a thin ribbon or bead onto the bristles of a toothbrush, and can 'stand' upon the bristles for an amount of time.

Accordingly, some embodiments provide a toothpaste or gel composition that contains no fluoride, while some embodiments provide a toothpaste or gel composition that comprises an effective amount of fluoride (e.g., a source of fluoride ion) to help prevent or slow tooth decay. In any of these embodiments, the toothpaste or gel composition can provide for the general cleaning of the teeth as well as the overall oral cavity (e.g., gums, tongue, palate, lips, and/or teeth). In some embodiments, the amount of fluoride added to the toothpaste composition suitably comprises, for example, about 0.01% to about 0.5%, about 0.02% to about 0.5%, about 0.1% to about 0.5%, or about 0.2% to about 0.5% (inclusive of any and all amounts that fall between those recited values) of a source of fluoride. In embodiments the amount of fluoride provided in the composition is adequate to comply with various local requirements for fluoride-containing dentifrices such as, for example, the requirements of the U.S. or Canadian monographs. In some embodiments the amount of fluoride in the composition can range from about 500 ppm to about 1500 ppm, about 700 ppm to about 1250 ppm, about 800 ppm to about 1200 ppm, or about 850 ppm to about 1150 ppm. The fluoride in the compositions described herein can be provided by any suitable fluoride source and, in some embodiments, comprises a fluoride compound that has been approved by a regulatory agency for safety and efficacy. Examples of suitable fluorides are stannous fluoride, sodium fluoride, aminefluorides, sodium monofluorophosphate, and the like, or any suitable combination thereof.

Suitably, the toothpaste formulations described herein comprise a flavor agent or a combination of two or more flavor agents. A substantial variety of flavor agents are known. The flavor agent can be selected from any appropriate flavor agent known in the art and that can be formulated in a toothpaste composition. Flavor agents can include natural, nature-identical, and artificial flavorants and flavoring substances (e.g., oils, oleoresin, extracts, distillate, essence, and the like) that function primarily as a flavor and provide little or no nutritional value. Examples of a suitable flavor agent include fruit flavor such as, for example, melon, cherry, berry (e.g., raspberry, strawberry, blueberry, cranberry, etc.) banana, grape, citrus (e.g., orange, lemon, lime, grapefruit, etc.), pear, apple, pineapple, mango, passion fruit, papaya, coconut, and the like; mint such as, for example, peppermint, spearmint, wintergreen, and the like; herbal/savory/sweet (e.g., cinnamon, anise, sassafras, sarsaparilla, vanilla, chocolate, nutmeg, acacia, molasses, clove, honey, fennel, ginger, caraway, coriander, eucalyptus, rosemary, basil, oregano, thyme and the like). Combination of flavors can be performed by one of skill to achieve any desired flavor profile, (e.g., a mixed berry, fruit punch, tropical fruit, bubblegum, sweet mint, herbal mint, etc.). Other flavor agents/components can be added as desired (e.g., to provide aroma and taste nuance), and suitably in minor amounts. Such components include floral, earthy, woody, pine, herbal, tea-like, musty and cheesy aroma and taste nuances. One of skill in the art will be able to determine the amounts and combination of flavor components that can be added in order to achieve a desired flavor profile. Some embodiments provide for one or a plurality of flavoring agents in total amounts ranging between about 0.01% and about 5%, about 0.1% and about 3%, or about 1% and about 2%, by weight (inclusive of any amount falling between those numbers). One of skill will be able to determine a suitable amount of flavoring agent(s) based on the desired flavor/odor profile and the identity of the flavoring agent(s).

Some embodiments provide for sweetening agents in addition to or in place of one or more flavoring agents, which helps to make the composition more pleasant and palatable, particularly to children. In some instances a sweetener can also function as a humectant (e.g., sorbitol and glycerin) which have a sweetness level about 60% (or more) of table sugar. In such embodiments, the use of sorbitol or glycerin can require one or more flavoring agents to make the toothpaste palatable. Accordingly, the amount of the sweetener will be dependent on the sweetness level of the particular sweetener used in the formulation. Suitable examples of sweetening agents include saccharin, xylitol, sucralose, aspartame, isomalt, and the like. Some embodiments provide for a sweetener in amounts ranging between about 0.01% and about 35%, about 0.05% and about 20%, about 0.1% and about 15%, or about 0.1% and about 10%, by weight (inclusive of any ranges and amounts falling between those numbers). As will be appreciated by one of skill in the art, the amount of sweetener can vary depending on the particular sweetener used in the formulation. The relative sweetness of a number of sweetening agents are known in the art (e.g., aspartame is about 200 times as sweet as sugar; saccharin about 300-500 times, sucralose about 600 times, acesulfame about 200 times, and neotame about 8000 times).

Embodiments provide for polishing or abrasive materials, such as any suitable synthetic or natural abrasive material to gently remove plaque and/or biofilm from teeth. Because some embodiments of the toothpaste formulations described herein find use in the kits and delivery systems directed toward children, care should be taken in choosing abrasive materials that would provide adequate cleaning without unnecessary abrasiveness in such instances. Examples include silicas, hydrated silicas, aluminas, calcium carbonates, sodium bicarbonate (baking soda) dicalciumphosphates, calcium pyrophosphates, hydroxyapatites, trimetaphosphates, insoluble hexametaphosphates, and also including agglomerated particulate abrasive materials. Some embodiments provide for polishing or abrasive agents in amounts ranging between about 0.1% and about 35%, about 1% and about 25%, about 2% and about 20%, or about 5% and about 20%, by weight (inclusive of any amount falling between those numbers).

In some embodiments, the compositions and formulations comprise one or a plurality of coloring agents that may be natural or synthetic dyes and pigments, suitable for use in the oral cavity of humans (e.g., adults and/or small children). Examples of colorants include dyes, lakes, and pigments and may include, but are not limited to, titanium dioxide, iron oxides, dyes such as, for example, FD&C Lakes, Carmine Lake, D&C Yellow 10, FD&C Blue no. 1, FD&C Blue no. 2, FD&C Red no. 3, FD&C Red no. 40, FD&C Yellow no. 5, FD&C Yellow no. 6, FD&C Green no. 3, alumina, talc, annatto extract, calcium carbonate, canthaxanthin, caramel, β-carotene, carmine, dihydroxyacetone, tumeric oleoresin, cochineal extract, gardenia yellow, gardenia blue, beet powder, grape skin extract, riboflavin, purple sweet potato, red sweet potato, chlorophyll-containing extracts, purple blend, carmine high tint, pearlescent pigments, natural colorants, and the like. Other examples of colorants are found in 21 C.F.R. §§73 and 74. Suitable quantities of coloring agent will depend largely on the individual characteristics of the agent, which is generally provided in an amount such that a pleasing color is generated. Some embodiments can include amounts ranging between about 0.0005% and about 5%, about 0.1% and about 2.0%, or about 0.5% and about 1.5%, by weight (inclusive of any amount falling between those numbers).

The embodiments provide for a humectant component, such as glycerine, glycerol, sorbitol, propylene glycol, xylitol, lactitol, and the like. As discussed herein, some embodiments provide for a humectant that can also function as a sweetener (e.g., xylitol, sorbitol, etc.). The amount of humectant is added such that the desired physical characteristic(s) of the toothpaste is achieved. Some embodiments provide for a humectant in amounts ranging between about 45% and about 85%, about 50% and about 80%, or about 60% and about 70%, by weight (inclusive of any amount falling between those numbers).

In some embodiments, the compositions and formulations can include binders and/or thickeners such as the non-limiting examples of sodium carboxymethyl-cellulose, cellulose, xanthan gum, gum arabic, karaya gum, bentonite, sodium alginate, methylcellulose, magnesium aluminum silicate, carrageenan, as well as synthetic polymers such as carbomers, polyacrylates, modified acrylic polymers, and carboxyvinyl polymers such as Carbopol®. Suitably, embodiments provide for a binder/thickener in amounts ranging between about 0.05% and about 2.5%, about 0.1% and about 2.0%, or about 0.5% and about 1.5%, by weight (inclusive of any amount falling between those numbers).

The toothpaste compositions also comprise an amount of water, suitably in an amount that is able to solubilize added salts and other water soluble compounds. Some embodiments provide for water in amounts ranging between about 5% and about 30%, about 5% and about 25%, or about 10% and about 20%, by weight (inclusive of any amount falling between those numbers).

Typically, one of skill will consider the combination of the amount of humectant, binder, and water in order to determine the appropriate viscosity and specific gravity of the toothpaste as described herein.

The aqueous based toothpaste compositions described herein can also comprise a buffering agent in an amount that is effective to maintain a stable formulation/composition pH (e.g., around physiological pH). Appropriate buffering agents and systems are known in the art and can be selected based on the nature of the agent and the other components in the toothpaste (e.g., so as to avoid any undesirable reactivity between components). Some embodiments provide for a buffering agent in amounts ranging between about 0.005% and about 0.4%, about 0.01% and about 0.3%, or about 0.05% and about 0.25%, by weight (inclusive of any amount falling between those numbers).

Embodiments of the toothpaste formulations described herein provide for other optional conventional ingredients. For example, the optional ingredients can include typical formulary components that are commonly used in toothpaste compositions, suitably children's toothpaste formulations, as are known in the art.

Some embodiments provide compositions that include surfactants, such as nonionic (such as ethylene oxide/propylene oxide block copolymers, e.g. Pluronic F 127), cationic, and zwitterionic or amphoteric surfactants. In some embodiments surfactants are nonionic surfactants and are used in small amounts, e.g. about 0.25% by weight.

Other optional ingredients that can be included are, for example, bleaching agents such as peroxy compounds (e.g. hydrogen peroxide, carbamide peroxide, organic peracids, potassium peroxydiphosphate, and the like); effervescing systems such as sodium bicarbonate/citric acid systems, color change systems, and the like, such as those known in the art. The compositions may, furthermore, comprise (colored) microcapsules which contain a solid or liquid core, to impart a speckled appearance to the compositions, particularly when the latter are in gel form.

Embodiments provide for compositions and formulations that are storable and/or have an extended shelf life capacity. Accordingly, embodiments relate to compositions that include one or more preservatives such as, for example, parabens (methyl, propyl, and the like), or sodium benzoate. Further, such embodiments can further comprise a container and/or packaging that is effective as a barrier (e.g., barrier(s)) to light, moisture, oxidation, etc.) that slows or prevents the uptake or incorporation of external elements in the composition.

One of skill in the art will appreciate that many combinations of the above-identified components can be used in order to arrive at a suitable formulation as a children's toothpaste. Suitably, the toothpaste is formulated such that its optional use with the tubes, delivery systems, and/or kits described herein provide for a product that is capable of producing a thin ribbon or bead of paste that can retain a desired shape or pattern and stand on the bristles of a toothbrush for a period of time (e.g., 30 seconds to about 10 minutes or more).

Toothpaste Manufacturing Processes

Toothpaste formulations and compositions described herein can be manufactured using techniques and equipment that are known and commonly used in the art. Manufacturing steps such as order of component addition, mixing temperatures (heating and/or cooling), mixing time, mixing speed, etc. can be driven by either by formulation or equipment requirements, or both. A number of parameters can be modified during the manufacturing process without substantial effect on the efficacy of the resulting product.

The manufacturing processes can further include separate steps for validating the resulting composition (e.g., the total amounts, ratios, and even distribution of composition components, measurement of amount of water or fluoride in the composition, etc.) using any known technique.

Some examples of equipment that can be useful in the manufacture of the compositions described herein include Hobart, Brogli, or other similar mixing equipment that allow for large scale mixing of viscous compositions. One of skill in the art will understand that alternative equipment and manufacturing process steps can be used that will result in an effective composition as described herein and will be apparent to one of ordinary skill in the art.

Merely for illustrative purposes a general sequence of manufacturing steps are provided below.

Weighing and Mixing

After transporting the raw materials into the factory, the ingredients are both manually and mechanically weighed. This ensures accuracy in the ingredients' proportions. Then the ingredients are mixed together in a mixing vessel. The temperature and humidity of the vessel can be monitored. Such factors can be used to ensure that the mix comes together correctly.

Filling the Tubes

Before tubes are filled with toothpaste, the tube itself passes under a blower and a vacuum to ensure cleanliness.

Dust and particles are blown out in this step. The tube is capped, and the opposite end is opened so the filling machine can load the paste.

After the ingredients are mixed together, the tubes are typically filled by a filling machine. To make sure the tube is aligned correctly, an optical device rotates the tube. Then the tube is filled by a descending pump. After it is filled, the end is sealed (or crimped) closed. The tube also gets a code stamped on it indicating where and when it was manufactured.

Packaging and Shipment

After tubes are filled, they are inserted into open paperboard boxes. This can be performed by hand or by automation.

The boxes are cased and shipped to warehouses and stores.

It is to be understood that the phraseology and terminology used herein is for the purpose of description and should not be regarded as limiting to the scope of the invention as claimed.

We claim:

1. A toothpaste delivery kit for use with a standard child sized toothbrush having a brush head defining a first width, the toothpaste delivery kit comprising:
    a first tube including a nozzle and containing a first product;
    a second tube including a nozzle and containing a second product;
    a package at least partially containing the first tube and the second tube therein;
    wherein the first and the second products are mixable and each comprise a composition including a flavoring agent, a coloring agent, a humectant, an abrasive, a buffering agent, a binder, a sweetener, and water, at least one of the flavoring agent or the coloring agent of the first product being different than at least one of the flavoring agent or the coloring agent of the second product;
    wherein the nozzle of first tube is configured to apply the first product in a first ribbon directly in contact with the brush head and the nozzle of the second tube is configured to apply the second product in a second ribbon directly in contact with the brush head such that the first ribbon and the second ribbon are disposed side-by-side on the bristles of the brush head; and
    wherein the first tube and the second tube each include a nozzle defining an output diameter that is less than half the first width.

2. The toothpaste delivery kit of claim 1, wherein the first tube and the second tube each includes a body made of deformable material, the tubes having a substantially elongated shape, and a tapered section extending from the body.

3. The toothpaste delivery kit of claim 1, wherein the nozzle includes a threaded portion, a collection chamber extending from the threaded portion, and an output orifice defining the output diameter.

4. The toothpaste delivery kit of claim 3, wherein the output diameter is between about 0.04 and about 0.2 inches.

5. The toothpaste delivery kit of claim 3, wherein the output diameter is between about 0.04 and about 0.1 inches.

6. The toothpaste delivery kit of claim 3, wherein the output diameter is between about 0.04 an about 0.06 inches.

7. The toothpaste delivery kit of claim 3, wherein the output diameter is about 0.06 inches.

8. The toothpaste delivery kit of claim 1, wherein the nozzle includes a substantially conical body defining the channel therethrough, the channel including a threaded portion having internally extending threads that couple to the tube, a collection chamber having a substantially conical shape, and an output orifice defining an output diameter through which the product is dispensed, and wherein the output diameter is between about 0.04 and about 0.2 inches.

9. The toothpaste delivery kit of claim 8, further comprising a cap coupled to the body and movable between an open and a closed position.

10. The toothpaste delivery kit of claim 9, wherein the cap includes a plug having a protrusion and an annular wall.

11. The toothpaste tube of claim 8, wherein the channel extends from the threaded portion to define the output orifice.

12. The toothpaste tube of claim 8, wherein the output orifice is substantially opposite the threaded portion.

13. The toothpaste delivery kit of claim 1, wherein the composition comprises a viscosity of about 80,000 to about 300,000 cps at approximately 25° C.

14. The toothpaste delivery kit of claim 13, wherein the composition comprises a specific gravity of about 1.20 to about 1.40 at approximately 25° C.

15. A toothpaste delivery kit comprising:
    a first tube including a nozzle and containing a first product, and wherein the first product comprises a composition including a flavoring agent, a coloring agent, a humectant, an abrasive, a buffering agent, a binder, a sweetener, and water;
    a second tube including a nozzle and containing a second product, and wherein the second product comprises a composition including a flavoring agent, a coloring agent, a humectant, an abrasive, a buffering agent, a binder, a sweetener, and water;
    a package at least partially containing the first tube and the second tube therein;
    wherein the nozzle of the first tube and the nozzle of the second tube each define an output orifice with an output diameter sized to apply the first product in a first ribbon and the second product in a second ribbon directly in contact with the same toothbrush head such that the first ribbon and the second ribbon are side-by-side on the toothbrush head.

* * * * *